United States Patent [19]

Meyers et al.

[11] Patent Number: 5,693,047
[45] Date of Patent: Dec. 2, 1997

US005693047A

[54] PRESS FIT INTRAMEDULLARY REAMER HEAD

[75] Inventors: John Meyers, Columbia City; James R. Toone, Fort Wayne; Mark Bryant, Auburn, all of Ind.

[73] Assignee: Zimmer, Inc., Warsaw, Ind.

[21] Appl. No.: 598,724

[22] Filed: Feb. 8, 1996

[51] Int. Cl.$^6$ ................................. A61B 17/16
[52] U.S. Cl. .............................. 606/80; 606/180
[58] Field of Search ........................ 606/79, 80, 81, 606/180; 279/102; 408/239 R

[56] References Cited

U.S. PATENT DOCUMENTS

| | | | |
|---|---|---|---|
| 726,388 | 4/1903 | Wysong | 279/102 |
| 2,325,691 | 8/1943 | Litwin et al. | 279/102 |
| 3,321,209 | 5/1967 | Sanders | 279/102 |
| 4,509,887 | 4/1985 | Hofling | 408/239 R |
| 5,499,984 | 3/1996 | Steiner et al. | |

Primary Examiner—Michael Buiz
Assistant Examiner—David O. Reip
Attorney, Agent, or Firm—Todd A. Dawson

[57] ABSTRACT

Abstract of the Disclosure Intramedullary reamers are well known in orthopaedic procedures for reaming out a tubular passage within a bone for accommodating an implant such as a femoral nail. The reamer head of this invention is designed to accommodate a press fit connection to a reamer shaft. Heretofore, such press fit connections placed a hoop stress on the neck of the shaft such that the hoop stress significantly exceeded the yield strength of the material. Therefore in such prior art heads, the neck of the head would begin to crack adjacent the opening of the neck. The reamer head of this invention substantially reduces the hoop stresses on the neck of the head at its opening and provides for a smoother transition of stresses along the neck by forming a counter bore through the neck while maintaining a satisfactory press fit connection between the head and the shaft.

1 Claim, 1 Drawing Sheet

PRESS FIT INTRAMEDULLARY REAMER HEAD

FIELD OF THE INVENTION

This invention relates to a press fit intramedullary reamer head and more particularly relates to a reamer head having a counter bore adjacent its press fit connection to a shaft.

SUMMARY OF THE INVENTION

Intramedullary reamers are well known in orthopaedic procedures for reaming out a tubular passage within a bone for accommodating an implant such as a femoral nail. The reamer head of this invention is designed to accommodate a press fit connection to a reamer shaft. Heretofore, such press fit connections placed a hoop stress on the neck of the shaft such that the hoop stress significantly exceeded the yield strength of the material. Therefore, in such prior art heads, the neck of the head would begin to crack adjacent the opening of the neck.

The reamer head of this invention substantially reduces the hoop stresses on the neck of head at its opening and provides for a smoother transition of stresses along the neck by forming a counter bore through the neck while maintaining a satisfactory press fit connection between the head and the shaft.

Accordingly, it is an object of the invention to provide for a novel press fit connection between a cylindrical drive shaft and a head.

Another object of the invention is to provide for a press fit reamer head having a counter bore through the neck to reduce the hoop stress at the neck opening.

Other objects of this invention will become apparent upon a reading of the following description taken with the accompanying drawings.

DESCRIPTION OF THE PREFERRED EMBODIMENT

The preferred embodiment herein described is not intended to be exhaustive or to limit the application to the precise form disclosed. Rather, it is chosen and described to enable others skilled in the art to utilize it teachings.

Figure 1:
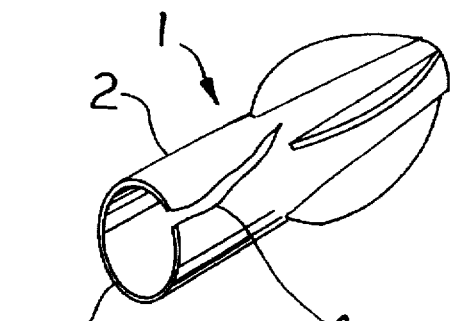
FIG. 1 is a perspective view of a prior art press fit reamer head (partially sectioned) illustrating typical damage to the neck.
Figure 2:
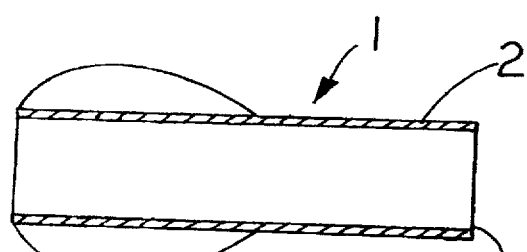
FIG. 2 is a longitudinal sectional view of the prior art reamer head of FIG. 1

FIGS. 1 and 2 illustrate a prior art press fit reamer head 1. The neck 2 of the head 1 includes a squared opening having corners with large radiuses. The inner dimensions of the neck are such that the interior side wall of the neck engage a drive shaft inserted therein in a mechanical press fit. Upon rotation of the drive shaft (not shown) the reamer head is rotated. However, it has been determined by the applicant that such a design, wherein the press fit extends the entire length of the neck, creates a very narrow stress transition zone. Therefore, the hoop stresses are concentrated about opening 3 of the neck 2. It has been found that the concentration of such stress can result in a hoop stress of around 78% of the yield strength of the material causing damage such as the formation of a crack 4.

Figure 3:
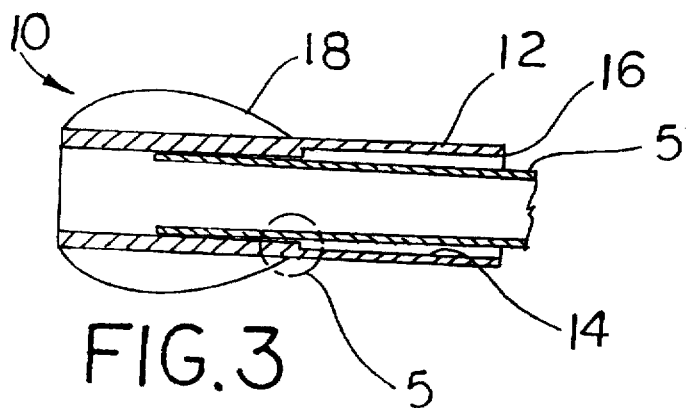
FIG. 3 is a sectional view of the reamer head of this invention with the reamer shaft inserted therein.
Figure 4:
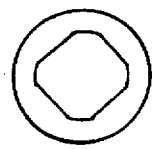
FIG. 4 is an end view of the reamer head of the invention.
Figure 5:
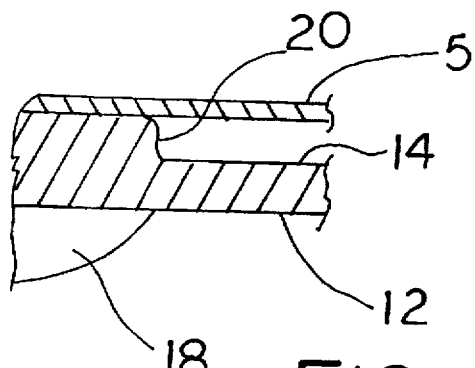
FIG. 5 is an enlarged view of the area circled in FIG. 3 and designated by numeral 5.

FIGS. 3–5 illustrate the reamer head 10 of the invention. As with the prior art reamer head 1, reamer head 10 includes a squared opening having large radiuses to accommodate drive shaft 5. As illustrated best in FIGS. 3 and 5, the interior of neck 12 includes a counter bored portion 14 such that the inner diameter of the neck adjacent opening 16 is larger than the inner diameter of the neck adjacent the fluted head portion 18. A transition area 20 is formed between the larger diameter and smaller diameters of the neck and fluted head portion. Therefore, shaft 5 forms a press fit with head 10 near the fluted head portion 18 and a loose fit with the neck adjacent opening 16. It should be understood that FIGS. 3 and 5 illustrate the loose fit in an exaggerated manner to illustrate the invention. In practice, the difference between the outer diameter of the shaft and the inner diameter of the neck adjacent opening 16 is approximately a millimeter.

Since the press fit between the shaft 5 and head 10 terminates at the transition area 20, which is spaced from opening 16 of the neck, the stresses generated during reaming are not concentrated at the opening. By forming the head in the manner described above, the Applicant has reduced the hoop stress at opening 16 from 78% of the material yield strength as seen in the prior art to 35% of the material yield strength. With the significant reduction of hoop stress concentration, the head of the invention has a reduced occurrence of crack formation at the neck.

It should be understood that the invention is not to be limited to the precise form disclosed, but may be modified within the keeping of the appended claims.

We claim:

1. In combination, a longitudinally extending reamer head and a drive shaft, said drive shaft having an outer diameter, said reamer head having a neck portion and a head portion having a longitudinal bore extending therethrough, wherein the inner diameter of a portion of the bore adjacent the neck portion is larger than the inner diameter of a portion of the bore adjacent the head portion, the portion of the bore adjacent the head portion having a smaller inner diameter forms a press fit with the drive shaft, the portion of the bore adjacent the neck portion having a larger inner diameter forms a loose fit with the drive shaft.

* * * * *